US007105174B2

(12) United States Patent
Rudnic et al.

(10) Patent No.: US 7,105,174 B2
(45) Date of Patent: Sep. 12, 2006

(54) MULTIPLE-DELAYED RELEASE ANTI-NEOPLASTIC PRODUCT, USE AND FORMULATION THEREOF

(75) Inventors: Edward M. Rudnic, N. Potomac, MD (US); James D. Isbister, Potomac, MD (US); Donald J. Treacy, Jr., Annapolis, MD (US); Sandra E. Wassink, Frederick, MD (US)

(73) Assignee: Advancis Pharmaceutical Corporation, Germantown, MD (US)

( * ) Notice: Subject to any disclaimer, the term of this patent is extended or adjusted under 35 U.S.C. 154(b) by 0 days.

(21) Appl. No.: 10/211,035

(22) Filed: Aug. 2, 2002

(65) Prior Publication Data

US 2003/0104054 A1 Jun. 5, 2003

Related U.S. Application Data

(63) Continuation-in-part of application No. 09/791,905, filed on Feb. 22, 2001, now abandoned, which is a continuation-in-part of application No. 09/687,229, filed on Oct. 13, 2000, now abandoned, which is a continuation-in-part of application No. 09/687,235, filed on Oct. 13, 2000, now abandoned.

(51) Int. Cl.
*A61K 9/00* (2006.01)
*A61K 9/48* (2006.01)
*A61K 9/20* (2006.01)
*A61K 9/22* (2006.01)
*A61K 9/14* (2006.01)

(52) U.S. Cl. ............... 424/400; 424/451; 424/464; 424/468; 424/489; 424/502

(58) Field of Classification Search ............ 424/422, 424/430, 427, 437, 436, 443, 464, 465, 468, 424/480, 400, 451, 489, 502
See application file for complete search history.

(56) References Cited

U.S. PATENT DOCUMENTS

| 4,435,173 | A | 3/1984 | Siposs et al. ............ 609/155 |
|---|---|---|---|
| 4,616,008 | A | 10/1986 | Hirai et al. ............ 514/200 |
| 4,794,001 | A | 12/1988 | Mehta et al. ............ 424/458 |
| 4,831,025 | A | 5/1989 | Godtfredsen et al. ....... 514/195 |
| 4,904,476 | A * | 2/1990 | Mehta et al. |
| 4,915,953 | A | 4/1990 | Jordan et al. ............ 424/473 |
| 4,971,805 | A | 11/1990 | Kitanishi et al. ......... 424/494 |
| 5,011,692 | A | 4/1991 | Fujioka et al. ............ 424/426 |
| 5,110,597 | A | 5/1992 | Wong et al. ............ 424/438 |
| 5,213,808 | A | 5/1993 | Bar-Shalom et al. ....... 424/473 |
| 5,229,131 | A | 7/1993 | Amidon et al. ............ 424/451 |
| 5,395,626 | A | 3/1995 | Kotwal et al. ............ 424/472 |
| 5,401,512 | A | 3/1995 | Rhodes et al. ............ 424/458 |
| 5,414,014 | A | 5/1995 | Schneider et al. ......... 514/535 |
| 5,445,829 | A | 8/1995 | Paradissis et al. ......... 424/480 |
| 5,462,747 | A | 10/1995 | Radebaugh et al. ........ 424/465 |
| 5,472,708 | A * | 12/1995 | Chen |
| 5,508,040 | A | 4/1996 | Chen ..................... 424/451 |
| 5,567,441 | A | 10/1996 | Chen ..................... 424/494 |
| 5,672,359 | A | 9/1997 | Digenis et al. ............ 424/463 |
| 5,719,132 | A * | 2/1998 | Lin et al. |
| 5,827,531 | A | 10/1998 | Morrison et al. .......... 424/450 |
| 5,840,329 | A | 11/1998 | Bai ..................... 424/458 |
| 5,877,243 | A | 3/1999 | Sarangapani .............. 524/139 |
| 5,910,322 | A | 6/1999 | Rivett et al. ............ 424/484 |
| 6,027,748 | A | 2/2000 | Conte et al. ............ 424/458 |
| 6,132,771 | A | 10/2000 | Depui et al. ............ 424/468 |
| 6,294,199 | B1 | 9/2001 | Conley et al. ............ 424/468 |
| 6,358,525 | B1 | 3/2002 | Guo et al. ............ 424/464 |
| 2001/0046984 | A1 | 11/2001 | Rudnic et al. ......... 514/210.09 |
| 2001/0048944 | A1 | 12/2001 | Rudnic et al. ............ 424/468 |
| 2002/0004070 | A1 | 1/2002 | Rudnic et al. ............ 424/468 |
| 2002/0004499 | A1 | 1/2002 | Rudnic et al. ............ 514/192 |

FOREIGN PATENT DOCUMENTS

| WO | WO 94/27557 | 12/1994 |
|---|---|---|
| WO | WO 95/20946 | 8/1995 |
| WO | WO 96/04908 | 2/1996 |
| WO | WO 98/22091 | 5/1998 |

* cited by examiner

*Primary Examiner*—Humera N. Sheikh
(74) *Attorney, Agent, or Firm*—Elliot M. Olstein; Raymond E. Stauffer

(57) ABSTRACT

An anti-neoplastic product is comprised of at least three delayed release dosages forms, each of which has a different release profile, with the $C_{max}$ for the anti-neoplastic product being reached in less than about twelve hours after initial release of anti-neoplastic from the product.

37 Claims, No Drawings

MULTIPLE-DELAYED RELEASE ANTI-NEOPLASTIC PRODUCT, USE AND FORMULATION THEREOF

This application is a continuation-in-part of U.S. application Ser. No. 09/791,905, filed on Feb. 22, 2001 now abandoned, which is a continuation-in-part of U.S. application Ser. No. 09/687,229, filed on Oct. 13, 2000 now abandoned, which is a continuation-in-part of U.S. application Ser. No. 09/687,235, filed on Oct. 13, 2000, now abandoned.

This invention relates to an anti-neoplastic product, as well as the use and formulation thereof.

A wide variety of anti-neoplastics have been used, and will be used, in order to combat cancer. In general, such anti-neoplastics can be administered by a repeated dosing of immediate release dosage forms, which results in poor compliance or as a controlled release formulation (slow release) at higher administered doses. The present invention is directed to providing for an improved anti-neoplastic product.

In accordance with one aspect of the present invention, there is provided an anti-neoplastic pharmaceutical product which is comprised of at least two, preferably at least three, anti-neoplastic dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the dosage forms each start release of the anti-neoplastic contained therein at different times after administration of the anti-neoplastic product.

Thus, in accordance with an aspect of the present invention, there is provided a single or unitary anti-neoplastic product that has contained therein at least two, preferably at least three anti-neoplastic dosage forms, each of which has a different release profile, whereby the anti-neoplastic contained in each of such dosage forms is released at different times.

In accordance with a further aspect of the invention, the anti-neoplastic product may be comprised of at least four different dosage forms, each of which starts to release the anti-neoplastic contained therein at different times after administration of the anti-neoplastic product.

The anti-neoplastic product generally does not include more than five dosage forms with different release times.

In accordance with a preferred embodiment, the anti-neoplastic product has an overall release profile such that when administered the maximum serum concentration of the total anti-neoplastic released from the product is reached in less than twelve hours, preferably in less than eleven hours in each case after initial release of the anti-neoplastic. In an embodiment, the maximum serum concentration of the total anti-neoplastic released from the anti-neoplastic product is achieved no earlier than four hours after initial release of the anti-neoplastic.

In accordance with one preferred embodiment of the invention, there are at least three dosage forms, each of which is a delayed release dosage form (which may be a pH sensitive or a non-pH sensitive delayed dosage form, depending on the type of anti-neoplastic product). More particularly, the anti-neoplastic release from the second of the at least three dosage forms achieves a $C_{max}$ (maximum serum concentration in the serum) at a time after the anti-neoplastic released from the first of the at least three dosage forms achieves a $C_{max}$ in the serum, and the anti-neoplastic released from the third dosage form achieves a $C_{max}$ in the serum after the $C_{max}$ of anti-neoplastic released from the second dosage form. As used herein first, second, third, etc., refers to the order in which anti-neoplastic is released from the dosage form.

In one embodiment, the second of the at least two dosage forms initiates release of the anti-neoplastic contained therein at least one hour after the first dosage form initiates release, with the initiation of the release therefrom generally occurring no more than six hours after initiation of release of anti-neoplastic from the first dosage form of the at least three dosage forms.

In general, the first dosage form produces a $C_{max}$ for the anti-neoplastic released therefrom within from about 0.5 to about 2 hours after initiation of release, with the second dosage form of the at least three dosage forms producing a $C_{max}$ for the anti-neoplastic released therefrom in no more than about four hours after initiation of release from the first dosage form. Thus, $C_{max}$ for the second dosage form is achieved after $C_{max}$ for the first dosage form and generally in no more than about 2 to about 3.5 hours after $C_{max}$ is achieved from the first dosage form. In general, the $C_{max}$ for such second dosage form is achieved no earlier than two hours after initiation of release from the first dosage form; however, it is possible within the scope of the invention to achieve $C_{max}$ in a shorter period of time.

As hereinabove indicated, the anti-neoplastic product may contain at least three or at least four or more different dosage forms. For example, if the anti-neoplastic product includes a third dosage form, the anti-neoplastic released therefrom reaches a $C_{max}$ at a time later than the $C_{max}$ is achieved for the anti-neoplastic released from each of the first and second dosage forms. In a preferred embodiment, release of anti-neoplastic from the third dosage form is started after initiation of release of anti-neoplastic from both the first dosage form and the second dosage form. In one embodiment, $C_{max}$ for anti-neoplastic release from the third dosage form is achieved within eight hours after initiation of release from the first dosage form.

In general, the first dosage form initiates release of anti-neoplastic at a time later than anti-neoplastic would be released from an immediate release dosage form. For example, the first dosage form would initiate release within 1 to four hours after administration of the product.

In another embodiment, the anti-neoplastic product contains at least four delayed release dosage forms, with each of the at least four dosage forms having different release profiles, whereby the anti-neoplastic release from each of the at least four different dosage forms achieves a $C_{max}$ at a different time.

As hereinabove indicated, in a preferred embodiment, irrespective of whether the anti-neoplastic contains at least two or at least three or at least four different delayed release dosage forms each with a different release profile, $C_{max}$ for all the anti-neoplastic released from the anti-neoplastic product is achieved in less than twelve hours after release is initiated from the first dosage form., and more generally is achieved in less than eleven hours.

In a preferred embodiment, the anti-neoplastic product is a once a day product, whereby after administration of the anti-neoplastic product, no further product is administered during the day; i.e., the preferred regimen is that the product is administered only once over a twenty-four hour period. Thus, in accordance with the present invention, there is a single administration of an anti-neoplastic product with the anti-neoplastic being released in a manner such that overall anti-neoplastic release is effected with different release profiles in a manner such that the overall $C_{max}$ for the anti-neoplastic product is reached in less than twelve hours after first release of anti-neoplastic. The term single administration means that the total anti-neoplastic administered over a twenty-four hour period is administered at the same time, which can be a single tablet or capsule or two or more thereof, provided that they are administered at essentially the same time.

Applicant has found that a single dosage anti-neoplastic product comprised of at least three anti-neoplastic dosage forms each having a different release profile is an improvement over a single dosage anti-neoplastic product comprised of an anti-neoplastic dosage form having a single release profile. Each of the dosage forms of anti-neoplastic in a pharmaceutically acceptable carrier may have one or more anti-neoplastics and each of the dosage forms may have the same anti-neoplastic or different anti-neoplastics.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of anti-neoplastic may occur. Such "leakage" is not "release" as used herein.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, anti-neoplastic release from such fourth dosage form may be initiated prior to or after release from the second or third dosage form.

The anti-neoplastic product of the present invention, as hereinabove described, may be formulated for administration by a variety of routes of administration. For example, the anti-neoplastic product may be formulated in a way that is suitable for topical administration; administration in the eye or the ear; rectal or vaginal administration; as nose drops; by inhalation; as an injectable; or for oral administration. In a preferred embodiment, the anti-neoplastic product is formulated in a manner such that it is suitable for oral administration.

For example, in formulating the anti-neoplastic product for topical administration, such as by application to the skin, the at least two different dosage forms, each of which contains an anti-neoplastic, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an anti-neoplastic product in the form of a patch, which includes anti-neoplastic dosage forms having different release profiles, as hereinabove described.

In addition, the anti-neoplastic product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the anti-neoplastic product with at least three different dosage forms with different release profiles may be formulated for rectal or vaginal administration, as known in the art. This may take the form of a cream or emulsion, or other dissolvable dosage form similar to those used for topical administration.

As a further embodiment, the anti-neoplastic product may be formulated for use in inhalation therapy by coating the particles and micronizing the particles for inhalation.

In a preferred embodiment, the anti-neoplastic product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary anti-neoplastic product. Thus, for example, anti-neoplastic products may include a first dosage form in the form of a tablet that is an immediate release tablet, and may also include two or more additional tablets, each of which provides for a delayed release of the anti-neoplastic, as hereinabove described, whereby the $C_{max}$ of the anti-neoplastic released from each of the tablets is reached at different times, with the $C_{max}$ of the total anti-neoplastic released from the anti-neoplastic product being achieved in less than twelve hours after anti-neoplastic is first released.

The formulation of an anti-neoplastic product including at least three dosage forms with different release profiles for different routes of administration is deemed to be within the skill of the art from the teachings herein. As known in the art, with respect to delayed release, the time of release can be controlled by the concentration of anti-neoplastics in the coating and/or the thickness of the coating.

In formulating an anti-neoplastic product in accordance with the invention, in one embodiment, the first dosage form of the product generally provides from about 20% to about 50% of the total dosage of anti-neoplastic to be delivered by the product, with such first dosage form generally providing at least 25% of the total dosage of the anti-neoplastic to be delivered by the product. In many cases, the first dosage form provides from about 20% to about 30% of the total dosage of anti-neoplastic to be delivered by the product; however, in some cases it may be desirable to have the first dosage form provide for about 45% to about 50% of the total dosage of anti-neoplastic to be delivered by the product.

The remaining dosage forms deliver the remainder of the anti-neoplastic. In one embodiment, each of the delayed release dosage forms after the first delayed release dosage form may provide about equal amounts of anti-neoplastic; however, they may also be formulated so as to provide different amounts.

In accordance with the present invention, each of the dosage forms contains the same anti-neoplastic; however, each of the dosage forms may contain more than one anti-neoplastic.

In one embodiment, where the composition contains three delayed release components, the first component provides from 20% to 35% (preferably 20% to 30%), by weight, of the total anti-neoplastic; where there is four delayed release components, the first delayed release component provides from 15% to 30%, by weight, of the total anti-neoplastic; and where there are five delayed release components, the first delayed release component provides from 10% to 25%, by weight, of the total anti-neoplastic.

With respect to the delayed release components, where there are three delayed release components, the second delayed release component provides from 30% to 60%, by weight, of the total anti-neoplastic provided by the second and third delayed release components with the third delayed release component providing the remainder of the anti-neoplastic.

Where there are four delayed release components, the second released component provides 20% to 35% by weight of the total anti-neoplastic provided by the second, third and fourth delayed release components, the next in time delayed release component provides from 20% to 40%, by weight, of the anti-neoplastic provided by the second, third and fourth delayed release components and the last in time providing the remainder of the anti-neoplastic provided by the second, third and fourth delayed release components.

When there are five delayed release components, the second delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total anti-neoplastic provided by the second, third, fourth and fifth delayed release components.

An Immediate Release Component

The immediate release portion of this system can be a mixture of ingredients that breaks down quickly after administration to release the anti-neoplastic. This can take the form of either a discrete pellet or granule that is mixed in with, or compressed with, the other three components.

The materials to be added to the anti-neoplastics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000–10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The Non-pH Sensitive Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose, hydroxypropylmethylcellulose, hydroxypropylcellulose, hydroxyethylcellulose, carboxymethylcellulose, methylcellulose, nitrocellulose, Eudragit R, and Eudragit RL, Carbopol, or polyethylene glycols with molecular weights in excess of 8,000 daltons.

These materials can be present in concentrations from 4–20% (W/W).

As hereinabove indicated, the units comprising the anti-neoplastic composition of the present invention can be in the form of discrete pellets or particles contained in the capsule, or particles embedded in a tablet or suspended in a liquid suspension.

The anti-neoplastic composition of the present invention may be administered, for example, by any of the following routes of administration: sublingual, transmucosal, transdermal, parenteral, etc., and preferably is administered orally. The composition includes a therapeutically effective amount of the anti-neoplastic, which amount will vary with the anti-neoplastic to be used, the cancer to be treated, and the number of times that the composition is to be delivered in a day. The composition is administered to a host in an amount effective for treating a cancer The following are representative examples of agents for the treatment of cancer that may be used in accordance with the invention: carboplatin, busulfan, cisplatin, thiotepa, melphalan hydrochloride, cyclophosphamide, ifosfamide, chlorambucil, mechlorethamine hydrochloride, carmustine, lomustine, streptozocin, polifeprosan 20, dexrazoxane, dronabinol, granisetron hydrochloride, fluconazole, erythropoietin, octreotide acetate, pilocarpine hydrochloride, etidronate disodium, pamidronate disodium, allopurinol sodium, amifostine, filgrastim, mesna, ondansetron hydrochloride, dolasetron mesylate, leucovorin calcium, sargramostim, levamisole hydrochloride, doxorubicin hydrochloride, idarubicin hydrochloride, mitomycin, daunorubicin citrate, plicamycin, daunorubicin hydrochloride, bleomycin sulfate, mitoxantrone hydrochloride, valrubicin, dactinomycin, fludarabine phosphate, cytarabine, mercaptopurine, thioguanine, methotrexate sodium, cladribine, floxuridine, capecitabine, anastrozole, bicalutamide, tamoxifen citrate, testolactone, nilutamide, methyltestosterone, flutamide, toremifene citrate, goserelin acetate, estramustine phosphate sodium, ethinyl estradiol, esterified estrogen, leuprolide acetate, conjugated estrogens, megestrol acetate, aldesleukin, medroxyprogesterone acetate, dacarbazine, hydroxyurea, etoposide phosphate, megestrol acetate, paclitaxel, etoposide, teniposide, trastuzumab, rituximab, vinorelbine tartrate, denileukin diftitox, gemcitabine hydrochloride, vincristine sulfate, vinblastine sulfate, asparaginase, edrophonium chloride, bacillus calmette and guerin, irinotecan hydrochloride, pegaspargase, docetaxel, interferon alfa-2a, recombinant, tretinoin, porfimer sodium, interferon alfa-2b, recombinant, procarbazine hydrochloride, topotecan hydrochloride, altretamine, fluorouracil, prednisolone sodium phosphate, cortisone acetate, dexamethasone, dexamethasone sodium sulfate, dexamethasone acetate, hydrocortisone sodium phosphate, hydrocortisone, prednisolone, methylprednisolone sodium succinate, betamethasone sodium phosphate, betamethasone acetate, letrozole, mithramycin, mitotane, pentostatin, perfosfamide, raloxifene The invention will be further described with respect to the following examples; however, the scope of the invention is not limited thereby. All percentages in this specification, unless otherwise specified, are by weight.

Non-pH Sensitive Delayed Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| | Ingredient | Conc. (% W/W) |
|---|---|---|
| Example 1: | Fluorouracil | 65% (W/W) |
| | Microcrystalline cellulose | 20 |
| | Polyox | 7.5 |
| | Croscarmellose sodium | 7.5 |
| Example 2: | Fluorouracil | 55% (W/W) |
| | Microcrystalline cellulose | 25 |
| | Polyox | 10 |
| | Glyceryl monooleate | 10 |
| Example 3: | Fluorouracil | 75% (W/W) |
| | Polyox | 10 |
| | Hydroxypropylcellulose | 5 |
| | Croscarmellose sodium | 10 |
| Example 4: | Dexamethasone | 65% (W/W) |
| | Microcrystalline cellulose | 20 |
| | Polyox | 7.5 |
| | Croscarmellose sodium | 7.5 |
| Example 5: | Dexamethasone | 55% (W/W) |
| | Microcrystalline cellulose | 25 |
| | Polyox | 10 |
| | Glyceryl monooleate | 10 |
| Example 6: | Dexamethasone | 75% (W/W) |
| | Polyox | 10 |
| | Hydroxypropylcellulose | 5 |
| | Croscarmellose sodium | 10 |
| Example 7: | Valrubicin | 65% (W/W) |
| | Microcrystalline cellulose | 20 |
| | Polyox | 7.5 |
| | Croscarmellose sodium | 7.5 |
| Example 8: | Valrubicin | 55% (W/W) |
| | Microcrystalline cellulose | 25 |

-continued

| | Ingredient | Conc. (% W/W) |
|---|---|---|
| | Polyox | 10 |
| | Glyceryl monooleate | 10 |
| Example 9: | Valrubicin | 75% (W/W) |
| | Polyox | 10 |
| | Hydroxypropylcellulose | 5 |
| | Croscarmellose sodium | 10 |
| Example 10: | Tretinoin | 65% (W/W) |
| | Microcrystalline cellulose | 20 |
| | Polyox | 7.5 |
| | Croscarmellose sodium | 7.5 |
| Example 11: | Tretinoin | 55% (W/W) |
| | Microcrystalline cellulose | 25 |
| | Polyox | 10 |
| | Glyceryl monooleate | 10 |
| Example 12: | Tretinoin | 75% (W/W) |
| | Polyox | 10 |
| | Hydroxypropylcellulose | 5 |
| | Croscarmellose sodium | 10 |

Enteric Release Component

Formulate the ingredients by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

| | Ingredient | Conc. (% W/W) |
|---|---|---|
| Example 13: | | |
| | Fluorouracil | 65% (W/W) |
| | Microcrystalline cellulose | 20 |
| | Cellulose Acetate Pthalate | 15 |
| Example 14: | | |
| | Fluorouracil | 55% (W/W) |
| | Microcrystalline cellulose | 25 |
| | Cellulose Acetate Pthalate | 10 |
| | Hydroxypropylmethylcellulose | 10 |
| Example 15: | | |
| | Fluorouracil | 65% (W/W) |
| | Polyox | 20 |
| | Hydroxypropylcellulose pthalate | 10 |
| | Eudragit L 30D | 5 |
| Example 16: | | |
| | Fluorouracil | 40% (W/W) |
| | Microcrystalline Cellulose | 40 |
| | Cellulose Acetate Pthalate | 10 |
| Example 17: | | |
| | Dexamethasone | 70% (W/W) |
| | Hydroxypropylcellulose pthalate | 15 |
| | Croscarmellose sodium | 10 |
| Example 18: | | |
| | Dexamethasone | 75% (W/W) |
| | Polyethylene glycol 2000 | 10 |
| | Eudragit L 30D | 15 |
| Example 19: | | |
| | Dexamethasone | 40% (W/W) |
| | Lactose | 50 |
| | Eudragit L 30D | 10 |

| Ingredient | Conc. (% W/W) |
|---|---|
| Example 20: | |
| Valrubicin | 65% (W/W) |
| Microcrystalline Cellulose | 20 |
| Eudragit L 30D | 10 |
| Example 21: | |
| Valrubicin | 75% (W/W) |
| Microcrystalline Cellulose | 15 |
| Hydroxypropylcellulose pthalate | 10 |
| Example 22: | |
| Valrubicin | 80% (W/W) |
| Lactose | 10 |
| Eudragit L 30D | 10 |
| Example 23: | |
| Valrubicin | 70% (W/W) |
| Polyethylene glycol 4000 | 20 |
| Cellulose acetate pthalate | 10 |
| Example 24: | |
| Tretinoin | 60% (W/W) |
| Polyethylene glycol 2000 | 10 |
| Lactose | 20 |
| Eudragit L 30D | 10 |
| Example 25: | |
| Tretinoin | 70% (W/W) |
| Microcrystalline cellulose | 20 |
| Cellulose acetate pthalate | 10 |

Sustained Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

| Ingredient | Conc. (% W/W) |
|---|---|
| Example 26: | |
| Fluorouracil | 65% (W/W) |
| Ethylcellulose | 20 |
| Polyox | 10 |
| Hydroxypropylmethylcellulose | 5 |
| Example 27: | |
| Fluorouracil | 55% (W/W) |
| Lactose | 25 |
| Polyox | 10 |
| Glyceryl monooleate | 10 |
| Example 28: | |
| Fluorouracil | 70% (W/W) |
| Polyox | 20 |
| Hydroxypropylcellulose | 10 |
| Example 29: | |
| Dexamethasone | 75% (W/W) |
| Lactose | 15 |
| Hydroxypropylcellulose | 5 |
| Ethylcellulose | 5 |

| Ingredient | Conc. (% W/W) |
|---|---|
| Example 30: | |
| Dexamethasone | 75% (W/W) |
| Polyethylene glycol 4000 | 10 |
| Lactose | 10 |
| Eudragit RL 30D | 5 |
| Example 31: | |
| Dexamethasone | 80% (W/W) |
| Polyethylene glycol 8000 | 10 |
| Hydroxypropylmethylcellulose | 5 |
| Eudgragit RS 30D | 5 |
| Example 32: | |
| Valrubicin | 75% (W/W) |
| Hydroxyethylcellulose | 10 |
| Polyethylene glycol 4000 | 10 |
| Hydroxypropylcellulose | 5 |
| Example 33: | |
| Valrubicin | 75% (W/W) |
| Lactose | 10 |
| Povidone (PVP) | 10 |
| Polyethylene glycol 2000 | 5 |
| Example 34: | |
| Tretinoin | 75% (W/W) |
| Polyethylene glycol 4000 | 10 |
| Povidone (PVP) | 10 |
| Hydroxypropylcellulose | 5 |
| Example 35: | |
| Tretinoin | 75% (W/W) |
| Lactose | 15 |
| Polyethylene glycol 4000 | 5 |
| Polyvinylpyrrolidone | 5 |
| Example 36: | |
| Dexamethasone | 40% (W/W) |
| Eudragit RS 30D | 50 |
| Triethyl Citrate | 10 |
| Example 37: | |
| Dexamethasone | 50% (W/W) |
| Sureteric | 50 |
| Example 38: | |
| Dexamethasone | 50% (W/W) |
| Eudragit RA 30D | 45 |
| Triethyl Citrate | 5 |

All Delayed Release Three Pulses

EXAMPLE 39

Anti-Neoplastic Pellet Formulation and Preparation Procedure

Pellet Formulations

The composition of the Anti-neoplastic pellets provided in Table 1.

TABLE 1

Composition of Anti-neoplastic Pellets

| Component | Percentage (%) |
|---|---|
| Anti-neoplastic drug | 92 |
| Avicel PH 101 | 6.0 |
| Polyoxyl 35 Castor Oil* | 1.0 |
| Hydroxypropyl methylcellulose, NF* | 1.0 |

TABLE 1-continued

Composition of Anti-neoplastic Pellets

| Component | Percentage (%) |
| --- | --- |
| Purified Water | ** |
| Total | 100 |

*Hydroxypropyl methylcellulose and Cremaphor EL were added as a 2.9% w/w aqueous solution during wet massing.
**Removed during processing Preparation Procedure for Anti-Neoplastic Pellets
  Blend Anti-neoplastic and Avicel® PH 101 using a high shear mixer.
  Add the hydroxypropyl methylcellulose and Polyoxyl 35 Castor Oil binder solution slowly into the powder blend under continuous mixing.
  Extrude the wet mass using an LCI Bench Top Granulator. The diameter of the screen of the Bench Top Granulator is 0.8 mm.
  Spheronize the extrudate using a QJ-230 Spheronizer using a small cross section plate.
  Dry the spheronized pellets at 60° C. using a fluid bed dryer until the exhaust temperature reaches 40° C.
  Pellets between 20 and 40 Mesh were collected for further processing.

Anti-Neoplastic Pulse One Pellet Formulation and Preparation Procedure

Preparation of an AQOAT AS-LF Aqueous Coating Dispersion

Dispersion Formulation
  The composition of the aqueous AQOAT AS-LF aqueous coating dispersion applied to the Anti-neoplastic pellets is provided below in Table 2.

TABLE 2

AQOAT AS-LF Aqueous Coating Dispersion

| Component | Percentage (%) |
| --- | --- |
| AQOAT AS-LF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-LF Aqueous Dispersion
  Add triethyl citrate (TEC) to the purified water with stirring.
  Add the sodium lauryl sulfate (SLS) to the TEC dispersion with stirring and completely until completely dissolved.
  Add the AQOAT to the TEC/SLS dispersion and stir for at least 30 minutes.
  Add the talc to the AQOAT dispersion and until completely mixed and for at least 30 minutes.
  Screen the dispersion through a No. 60 mesh sieve prior to coating.
  Continue to stir the dispersion until the coating process is complete.

Coating Conditions for the Application of AQOAT AS-LF Aqueous Coating Dispersion
  The following coating parameters were used for coating of the AQOAT AS-LF film coating dispersion.

| Coating Equipment | STREA 1 ™ Table Top Laboratory Fluid Bed Coater |
| --- | --- |
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Anti-neoplastic pellets with AQOAT AS-LF film coating dispersion such that you apply 30% coat weight gain to the pellets.

Anti-Neoplastic Pulse Two Pellet Formulation and Preparation Procedure

Preparation of an AQOAT AS-HF Aqueous Coating Dispersion

Dispersion Formulation
  The composition of the aqueous AQOAT AS-HF aqueous coating dispersion applied to the Anti-neoplastic pellets is provided below in Table 3.

TABLE 3

AQOAT AS-HF Aqueous Coating Dispersion

| Component | Percentage (%) |
| --- | --- |
| AQOAT AS-HF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-HF Aqueous Dispersion
  Add triethyl citrate (TEC) to the purified water with stirring.
  Add the sodium lauryl sulfate (SLS) to the TEC dispersion with stirring and completely until completely dissolved.
  Add the AQOAT to the TEC/SLS dispersion and stir for at least 30 minutes.
  Add the talc to the AQOAT dispersion and until completely mixed and for at least 30 minutes.
  Screen the dispersion through a No. 60 mesh sieve prior to coating.
  Continue to stir the dispersion until the coating process is complete.

Coating Conditions for the Application of AQOAT AS-HF Aqueous Coating Dispersion
  The following coating parameters were used for coating of the AQOAT AS-HF film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Anti-neoplastic pellets with AQOAT AS-HF film coating dispersion such that you apply 30% coat weight gain to the pellets.

Anti-Neoplastic Pulse Three Pellet Formulation and Preparation Procedure

Preparation of an Eudragit® FS 30D Aqueous Coating Dispersion

Dispersion Formulation

The composition of the aqueous Eudragit® FS 30D dispersion applied to the Anti-neoplastic pellets is provided below in Table 4.

TABLE 4

Eudragit ® FS 30D Aqueous Coating Dispersion

| Component | Percentage (%) |
|---|---|
| Eudragit ® FS 30D | 54.8 |
| Triethyl Citrate | 0.9 |
| Talc | 3.3 |
| Purified Water* | 41.0 |
| Solid Content | 20.6 |
| Polymer Content | 16.4 |

*Removed during processing

Preparation Procedure for an Eudragit® FS 30D Aqueous Dispersion

Disperse triethyl citrate (TEC) in the purified water.
Add the talc in the triethyl citrate dispersion.
Homogenize the dispersion using a homogenizer.
Add slowly the Eudragit® FS 30D dispersion to the talc/TEC dispersion with stirring.
Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| Coating Equipment | STREA 1 ™ Table Top Laboratory Fluid Bed Coater |
|---|---|
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Anti-Neoplastic Tablets

Tableting of the Anti-Neoplastic Pellets

TABLE 5

Composition of Anti-neoplastic Tablets

| Component | Percentage (%) |
|---|---|
| Silicified microcrystalline cellulose | 21.6 |
| Lactose monohydrate | 13.0 |
| Povidone | 5.0 |
| Pulse One Pellets | 18.3 |
| Pulse Two Pellets | 18.3 |
| Pulse Three Pellets | 18.3 |
| Croscarmellose sodium | 5.0 |
| Magnesium stearate | 0.5 |
| Total | 100 |

Blend the silicified microcrystalline cellulose, lactose monohydrate, povidone, colloidal silicon dioxide and Anti-neoplastic coated pellets for 15 minutes in a tumble blender.
Add the magnesium stearate to the blender, and blend for 5 minutes.
Compress the blend on a rotary tablet press.
The fill weight should be adjusted to achieve the desired dose.

Encapsulation of the Anti-Neoplastic Pellets

Pellets are filled into hard gelatin capsules at a ratio of 33.4%:33.3%:33.3%: Pulse One, Pulse Two, and Pulse Three Pellets respectively. The capsule is filled with the three different pellets to achieve the desired dose.

The present invention is particularly advantageous in that there is provided an anti-neoplastic product which provides an improvement over twice a day administration of the anti-neoplastic and an improvement over a once a day administration of the anti-neoplastic.

Numerous modification and variations of the present invention are possible in light of the above teachings and therefore, within the scope of the appended claims the invention may be practiced otherwise than as particularly described.

All Delayed Release Four Pulses

EXAMPLE 40

Anti-Neoplastic Pellet Formulation and Preparation Procedure

Pellet Formulations

The composition of the Anti-neoplastic pellets provided in Table 6.

TABLE 6

Composition of Anti-neoplastic Pellets

| Component | Percentage (%) |
|---|---|
| Anti-neoplastic drug | 92 |
| Avicel PH 101 | 6.0 |
| Polyoxyl 35 Castor Oil* | 1.0 |
| Hydroxypropyl methylcellulose, NF* | 1.0 |
| Purified Water | ** |
| Total | 100 |

*Hydroxypropyl methylcellulose and Cremaphor EL were added as a 2.9% w/w aqueous solution during wet massing.
**Removed during processing

Preparation Procedure for Anti-Neoplastic Pellets

Blend Anti-neoplastic and Avicel® PH 101 using a high shear mixer.

Add the hydroxypropyl methylcellulose and Polyoxyl 35 Castor Oil binder solution slowly into the powder blend under continuous mixing.

Extrude the wet mass using an LCI Bench Top Granulator. The diameter of the screen of the Bench Top Granulator is 0.8 mm.

Spheronize the extrudate using a QJ-230 Spheronizer using a small cross section plate.

Dry the spheronized pellets at 60° C. using a fluid bed dryer until the exhaust temperature reaches 40° C.

Pellets between 20 and 40 Mesh were collected for further processing.

Anti-Neoplastic Pulse One Pellet Formulation and Preparation Procedure

Preparation of an AQOAT AS-LF Aqueous Coating Dispersion

Dispersion Formulation

The composition of the aqueous AQOAT AS-LF aqueous coating dispersion applied to the Anti-neoplastic pellets is provided below in Table 7.

TABLE 7

AQOAT AS-LF Aqueous Coating Dispersion

| Component | Percentage (%) |
|---|---|
| AQOAT AS-LF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-LF Aqueous Dispersion

Add triethyl citrate (TEC) to the purified water with stirring.

Add the sodium lauryl sulfate (SLS) to the TEC dispersion with stirring and completely until completely dissolved.

Add the AQOAT to the TEC/SLS dispersion and stir for at least 30 minutes.

Add the talc to the AQOAT dispersion and until completely mixed and for at least 30 minutes.

Screen the dispersion through a No. 60 mesh sieve prior to coating.

Continue to stir the dispersion until the coating process is complete.

Coating Conditions for the Application of AQOAT AS-LF Aqueous Coating Dispersion The following coating parameters were used for coating of the AQOAT AS-LF film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Anti-neoplastic pellets with AQOAT AS-LF film coating dispersion such that you apply 30% coat weight gain to the pellets.

Anti-Neoplastic Pulse Two Pellet Formulation and Preparation Procedure

Preparation of an Eudragit® L 30 D-55 Aqueous Coating Dispersion

Dispersion Formulation

The composition of the aqueous Eudragit L30D-55 aqueous coating dispersion applied to the Anti-neoplastic pellets is provided below in Table 8.

TABLE 8

Eudragit ® L 30 D-55 Aqueous Coating Dispersion

| Component | Percentage (%) |
|---|---|
| Eudragit ® L 30D-55 | 44.4 |
| Triethyl Citrate | 1.3 |
| Talc | 6.7 |
| Purified Water* | 47.6 |
| Solid Content | 21.3 |
| Polymer Content | 13.3 |

*Removed during processing

Preparation Procedure for an Eudragit® L 30D-55 Aqueous Dispersion

Disperse triethyl citrate (TEC) in the purified water.

Add the talc into the triethyl citrate dispersion.

Homogenize the dispersion using a homogenizer.

Add the TEC/talc dispersion to Eudragit L30D-55 latex dispersion and stir for at least 30 minutes.

Screen the dispersion through a No. 60 mesh sieve prior to coating.

Continue to stir the dispersion until the coating process is complete.

Coating Conditions for the Application of Eudragit L30D-55 Aqueous Coating Dispersion The following coating parameters were used for coating of the Eudragit® L 30 D-55 film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 45° C. |
| Outlet Air Temperature | 32 to 35° C. |
| Atomization Air Pressure | 1.6 Bar |
| Pump Rate | 3–4 gram per minute |

Coat Anti-neoplastic pellets with Eudragit L30 D-55 film coating dispersion such that you apply 30% coat weight gain to the pellets.

Anti-Neoplastic Pulse Three Pellets Formulation and Preparation Procedure

Preparation of an AQOAT AS-HF Aqueous Coating Dispersion

Dispersion Formulation

The composition of the aqueous AQOAT AS-HF aqueous coating dispersion applied to the Anti-neoplastic pellets is provided below in Table 9.

TABLE 9

AQOAT AS-HF Aqueous Coating Dispersion

| Component | Percentage (%) |
|---|---|
| AQOAT AS-HF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-HF Aqueous Dispersion

Add triethyl citrate (TEC) to the purified water with stirring.

Add the sodium lauryl sulfate (SLS) to the TEC dispersion with stirring and completely until completely dissolved.

Add the AQOAT to the TEC/SLS dispersion and stir for at least 30 minutes.

Add the talc to the AQOAT dispersion and until completely mixed and for at least 30 minutes.

Screen the dispersion through a No. 60 mesh sieve prior to coating.

Continue to stir the dispersion until the coating process is complete.

Coating Conditions for the Application of AQOAT AS-HF Aqueous Coating Dispersion The following coating parameters were used for coating of the AQOAT AS-HF film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Anti-neoplastic pellets with AQOAT AS-HF film coating dispersion such that you apply 30% coat weight gain to the pellets.

Anti-Neoplastic Pulse Four Pellet Formulation and Preparation Procedure

Preparation of an Eudragit® FS 30D Aqueous Coating Dispersion

Dispersion Formulation

The composition of the aqueous Eudragit® FS 30D dispersion applied to the Anti-neoplastic pellets is provided below in Table 10.

TABLE 10

Eudragit® FS 30D Aqueous Coating Dispersion

| Component | Percentage (%) |
|---|---|
| Eudragit® FS 30D | 54.8 |
| Triethyl Citrate | 0.9 |
| Talc | 3.3 |
| Purified Water* | 41.0 |
| Solid Content | 20.6 |
| Polymer Content | 16.4 |

*Removed during processing

Preparation Procedure for an Eudragit® FS 30D Aqueous Dispersion

Disperse triethyl citrate (TEC) in the purified water.

Add the talc in the triethyl citrate dispersion.

Homogenize the dispersion using a homogenizer.

Add slowly the Eudragit® FS 30D dispersion to the talc/TEC dispersion with stirring.

Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| Coating Equipment | STREA 1 ™ Table Top Laboratory Fluid Bed Coater |
|---|---|
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Anti-Neoplastic Tablets

Tableting of the Anti-Neoplastic Pellets

TABLE 11

Composition of Anti-neoplastic Tablets

| Component | Percentage (%) |
|---|---|
| Silicified microcrystalline cellulose | 21.5 |
| Lactose monohydrate | 13.0 |
| Povidone | 5.0 |
| Pulse One Pellets | 13.75 |
| Pulse Two Pellets | 13.75 |
| Pulse Three Pellets | 13.75 |
| Pulse Four Pellets | 13.75 |
| Croscarmellose sodium | 5.0 |
| Magnesium stearate | 0.5 |
| Total | 100 |

Blend the silicified microcrystalline cellulose, lactose monohydrate, povidone, colloidal silicon dioxide and Anti-neoplastic coated pellets for 15 minutes in a tumble blender.

Add the magnesium stearate to the blender, and blend for 5 minutes.

Compress the blend on a rotary tablet press.

The fill weight should be adjusted to achieve the desired dose.

Encapsulation of the Anti-Neoplastic Pellets

Pellets are filled into hard gelatin capsules at a ratio of 25%:25%:25%:25% Pulse One, Pulse Two, Pulse Three and Pulse Four Pellets respectively. The capsule is filled with the four different pellets to achieve the desired dose.

The present invention is particularly advantageous in that there is provided an anti-neoplastic product which provides an improvement over twice a day administration of the anti-neoplastic and an improvement over a once a day administration of the anti-neoplastic.

Numerous modification and variations of the present invention are possible in light of the above teachings and therefore, within the scope of the appended claims the invention may be practiced otherwise than as particularly described.

What is claimed is:

1. A once-a-day anti-neoplastic product comprising: first, second, and third anti-neoplastic dosage forms, each of said anti-neoplastic dosage forms comprising at least one anti-neoplastic and a pharmaceutically acceptable carrier, said first, second, and third anti-neoplastic dosage forms being delayed release dosage forms, and wherein each of said first, second, and third anti-neoplastic dosage forms initiates release of said at least one anti-neoplastic at different times, said once-a-day anti-neoplastic product further comprising a therapeutically effective amount of said at least one anti-neoplastic, said therapeutically effective amount being the total dosage of said at least one anti-neoplastic for a twenty-four hour period, and wherein said at least one anti-neoplastic released by said once-a-day anti-neoplastic product achieves Cmax in serum in less than twelve hours after the initial release of anti-neoplastic, said product being free of an immediate release dosage form.

2. The product of claim 1, wherein the Cmax for the product is reached no earlier than four hours after initial release of anti-neoplastic.

3. The product of claim 1, wherein the anti-neoplastic released from the first dosage form reaches a Cmax in serum within from about 0.5 hours to about 2 hours after initial release of anti-neoplastic.

4. The product of claim 1, wherein the anti-neoplastic released from the second dosage form reaches a Cmax in serum in no more than about 4 hours after initial release of anti-neoplastic.

5. The product of claim 1, wherein the anti-neoplastic released from the third dosage form reaches a Cmax in serum within 8 hours after initial release of anti-neoplastic.

6. The product of claim 1, wherein the first release dosage form contains at least 20% and no more than 50% of the total dosage of anti-neoplastic.

7. The product of claim 1, wherein the product is an oral dosage form.

8. The product of claim 7, wherein the anti-neoplastic released from the second dosage form reaches a Cmax in the serum after Cmax is reached in the serum for the anti-neoplastic released from the first dosage form.

9. The product of claim 8, wherein the anti-neoplastic released from the third dosage form reaches a Cmax in the serum after Cmax is reached in the serum for the anti-neoplastic released from the second dosage form.

10. The product of claim 9, wherein said second dosage form initiates release of said anti-neoplastic before said third dosage form, wherein said second dosage form provides from 30% to 60% by weight of the total anti-neoplastic released by said second and third dosage forms, and wherein said third dosage form provides the remainder of the total anti-neoplastic released by said second and third dosage forms.

11. The product of claim 1 further comprising a fourth anti-neoplastic dosage form, said fourth anti-neoplastic dosage form comprising at least one anti-neoplastic and a pharmaceutically acceptable carrier and wherein said at least one anti-neoplastic released from said fourth anti-neoplastic dosage form reaches a Cmax in the serum after Cmax is achieved in the serum for anti-neoplastic released from each of said first, second, and third dosage forms.

12. The product of claim 11, wherein said fourth anti-neoplastic dosage form is a delayed release dosage form.

13. The product of claim 12, wherein said second dosage form initiates release of said anti-neoplastic before said third dosage form, wherein said third dosage form initiates release of said anti-neoplastic before said fourth dosage form, wherein said second dosage form provides 20% to 35% by weight of the total anti-neoplastic released by said second, third, and fourth dosage forms, wherein said third dosage form provides from 20% to 40% by weight of the total anti-neoplastic released by said second, third, and fourth dosage forms, and wherein said fourth dosage form provides the remainder of the total anti-neoplastic released by said second, third, and fourth dosage forms.

14. The product of claim 11, wherein the anti-neoplastic released from the first dosage form reaches a Cmax in serum within from about 0.5 hours to about 2 hours after initial release of anti-neoplastic.

15. The product of claim 11, wherein the anti-neoplastic released from the second dosage form reaches a Cmax in serum in no more than about 4 hours after initial release of anti-neoplastic.

16. The product of claim 11, wherein the anti-neoplastic released from the third dosage form reaches a Cmax in serum within 8 hours after initial release of anti-neoplastic.

17. A process for treating a cancer in a host comprising: administering to a host the anti-neoplastic product of claim 1 once-a-day.

18. A process for treating a cancer in a host comprising: administering to a host the anti-neoplastic product of claim 2 once-a-day.

19. A process for treating a cancer in a host comprising: administering to a host the anti-neoplastic product of claim 3 once-a-day.

20. A process for treating a cancer in a host comprising: administering to a host the anti-neoplastic product of claim 4 once-a-day.

21. A process for treating a cancer in a host comprising: administering to a host the anti-neoplastic product of claim 5 once-a-day.

22. A process for treating a cancer in a host comprising: administering to a host the anti-neoplastic product of claim 6 once-a-day.

23. A process for treating a cancer in a host comprising: administering to a host the anti-neoplastic product of claim 7 once-a-day.

24. A process for treating a cancer in a host comprising: administering to a host the anti-neoplastic product of claim 8 once-a-day.

25. A process for treating a cancer in a host comprising: administering to a host the anti-neoplastic product of claim 9 once-a-day.

26. A process for treating a cancer in a host comprising: administering to a host the anti-neoplastic product of claim 10 once-a-day.

27. A process for treating a cancer in a host comprising: administering to a host the anti-neoplastic product of claim 11 once-a-day.

28. A process for treating a cancer in a host comprising: administering to a host the anti-neoplastic product of claim 12 once-a-day.

29. A process for treating a cancer in a host comprising: administering to a host the anti-neoplastic product of claim 13 once-a-day.

30. A process for treating a cancer in a host comprising: administering to a host the anti-neoplastic product of claim 14 once-a-day.

31. A process for treating a cancer in a host comprising: administering to a host the anti-neoplastic product of claim 15 once-a-day.

32. A process for treating a cancer in a host comprising: administering to a host the anti-neoplastic product of claim 16 once-a-day.

33. The once-a-day antineoplastic product of claim 1, wherein said at least one antineoplastic agent is in the form of a salt.

34. The once-a-day antineoplastic product of claim 11, wherein said at least one antineoplastic agent is in the form of a salt.

35. A process for treating a cancer in a host comprising: administering to a host the anti-neoplastic product of claim 33 once-a-day.

36. A process for treating a cancer in a host comprising: administering to a host the anti-neoplastic product of claim 34 once-a-day.

37. A process for treating a patient with an antineoplastic agent said process for treating comprising:

administering to a patient once-a-day an antineoplastic product, said product comprising: first, second, and third dosage forms, wherein each of said dosage forms includes at least one antineoplastic agent and a pharmaceutically acceptable carrier; said treating including delayed releases of antineoplastic from each of said first, second, and third dosage forms, said three delayed releases initiating release of antineoplastic at different times to produce a Cmax in serum of the total antineoplastic agent released from said antineoplastic product in less than about 12 hours from the initial release of antineoplastic agent; and said treating delivers the total dosage of said at least one antineoplastic agent for a twenty-four hour period.

* * * * *